US010605693B2

(12) United States Patent
Suzuki et al.

(10) Patent No.: US 10,605,693 B2
(45) Date of Patent: Mar. 31, 2020

(54) REACTION FORCE MEASURING DEVICE, DEGRADATION DIAGNOSING METHOD AND DEGRADATION DIAGNOSING DEVICE

(71) Applicant: BRIDGESTONE CORPORATION, Tokyo (JP)

(72) Inventors: Koji Suzuki, Hayama-machi (JP); Taisuke Kuroda, Yokohama (JP)

(73) Assignee: BRIDGESTONE CORPORATION, Tokyo (JP)

( * ) Notice: Subject to any disclaimer, the term of this patent is extended or adjusted under 35 U.S.C. 154(b) by 0 days.

(21) Appl. No.: 15/738,418

(22) PCT Filed: Jun. 30, 2016

(86) PCT No.: PCT/JP2016/003150
§ 371 (c)(1),
(2) Date: Dec. 20, 2017

(87) PCT Pub. No.: WO2017/002370
PCT Pub. Date: Jan. 5, 2017

(65) Prior Publication Data
US 2018/0180512 A1    Jun. 28, 2018

(30) Foreign Application Priority Data
Jun. 30, 2015    (JP) .................................. 2015-131865

(51) Int. Cl.
*G01M 5/00* (2006.01)
*G01N 3/20* (2006.01)
(Continued)

(52) U.S. Cl.
CPC ............. *G01M 5/0058* (2013.01); *G01L 5/00* (2013.01); *G01L 5/0028* (2013.01); *G01L 5/107* (2013.01); *G01N 3/20* (2013.01)

(58) Field of Classification Search
CPC ..... G01M 5/0058; G01L 5/107; G01L 5/0028; G01L 5/00; G01N 3/20
See application file for complete search history.

(56) References Cited

U.S. PATENT DOCUMENTS 2,283,730 A * 5/1942 Gardner ................... G01N 3/20
73/849
5,127,271 A * 7/1992 Sato ...................... G01M 5/0058
73/852
(Continued)

FOREIGN PATENT DOCUMENTS

CN    102879408 A    1/2013
CN    102928444 A    2/2013
(Continued)

OTHER PUBLICATIONS

International Search Report of PCT/JP2016/003150 dated Sep. 27, 2016.
(Continued)

*Primary Examiner* — Nathaniel T Woodward
(74) *Attorney, Agent, or Firm* — Sughrue Mion, PLLC

(57) ABSTRACT

Provided is a reaction force measuring device comprising: a receiving portion 12; a movable portion 13 arranged in a manner spaced from the receiving portion 12 and capable of moving toward the receiving portion 12, the movable portion having a sandwiching space a formed between itself and the receiving portion 12, into which sandwiching space a hose H can be inserted from a direction crossing a longitudinal direction of the hose; and a measuring portion 14 configured to measure a reaction force of the hose H generated when the hose is pressed and applied with a load as the movable portion 13 moves toward the receiving portion 12.

20 Claims, 4 Drawing Sheets

(51) Int. Cl.
*G01L 5/00* (2006.01)
*G01L 5/107* (2020.01)

(56) References Cited

U.S. PATENT DOCUMENTS

| | | | | |
|---|---|---|---|---|
| 5,287,757 A * | 2/1994 | Polaert | G01G 3/1402 | 177/211 |
| 5,767,671 A * | 6/1998 | McCoy | E21B 12/02 | 324/209 |
| 6,250,168 B1 * | 6/2001 | D'Aguanno | A63B 60/42 | 73/865.3 |
| 9,046,452 B1 * | 6/2015 | Huang | G01N 3/20 | |
| 2002/0108449 A1 * | 8/2002 | Kohli | G01M 5/0025 | 73/849 |
| 2007/0144632 A1 * | 6/2007 | Toyoda | C21D 8/0226 | 148/593 |
| 2008/0077332 A1 * | 3/2008 | Newman | G01N 3/32 | 702/34 |
| 2011/0154908 A1 * | 6/2011 | McKee | E21B 19/22 | 73/829 |
| 2013/0144481 A1 | 6/2013 | Syed et al. | | |
| 2016/0061688 A1 * | 3/2016 | Van Wittenberghe | G01M 3/2853 | 73/577 |
| 2016/0195460 A1 | 7/2016 | Stenvik et al. | | |

FOREIGN PATENT DOCUMENTS

| | | |
|---|---|---|
| CN | 103134691 A | 6/2013 |
| CN | 203337470 U | 12/2013 |
| DE | 102009028521 A1 | 2/2011 |
| EP | 3 121 584 A1 | 1/2017 |
| JP | 5770427 A | 4/1982 |
| JP | 04-001552 A | 1/1992 |
| JP | 4130241 A | 5/1992 |
| JP | 09-021736 A | 1/1997 |
| JP | 10-288575 A | 10/1998 |
| JP | 2003-337093 A | 11/2003 |
| JP | 2008-20320 A | 1/2008 |
| JP | 2010-025573 A | 2/2010 |
| JP | 2014-025862 A | 2/2014 |
| JP | 2014-98961 A | 5/2014 |
| WO | 2014/045695 A1 | 3/2014 |
| WO | 2015/023279 A1 | 2/2015 |
| WO | 2015/141232 A1 | 9/2015 |

OTHER PUBLICATIONS

Communication dated Jun. 6, 2018, from the European Patent Office in counterpart European Application No. 16817480.3.
Search Report dated Sep. 6, 2019 in Chinese Application No. 201680036046.6.

* cited by examiner

REACTION FORCE MEASURING DEVICE, DEGRADATION DIAGNOSING METHOD AND DEGRADATION DIAGNOSING DEVICE

CROSS REFERENCE TO RELATED APPLICATIONS

This application is a National Stage of International Application No. PCT/JP2016/003150 filed Jun. 30, 2016, claiming priority based on Japanese Patent Application No. 2015-131865 filed Jun. 30, 2015, the contents of all of which are incorporated herein by reference in their entirety.

TECHNICAL FIELD

This disclosure relates to: a reaction force measuring device for measuring a reaction force of a hose applied with a load; and a degradation diagnosing method and a degradation diagnosing device using the reaction force measuring device.

BACKGROUND

Conventionally, in construction machines, factory equipment, etc. for forming a flow path (e.g., oil path) for transporting a fluid at high temperature and high pressure (e.g., oil), a hose composed of a rubber layer with an inner circumferential side in contact with the fluid is used. This hose has at least a metallic wire layer and an inner tube rubber layer arranged on a circumferential side inner than this metallic wire layer. Examples include one constituted by respectively laminating the inner tube rubber layer, the metallic wire layer, an intermediate rubber layer and an outer coating rubber layer from a radial inner side to an outer side. Moreover, this hose is, for example, connected to a machine, device, etc. into which a fluid is transported, via a metallic mouthpiece attached to both ends of the hose.

During long-term use of the aforementioned hose, in particular, gradual thermal aging due to heat from the fluid, etc. of the rubber layer on the inner circumferential side is unavoidable, and if the rubber layer suffers from excessive thermal aging, there would be a defect due to degradation of the rubber layer, such as that the fluid inside the hose leaks from the mouthpiece. In order to avoid occurrence of such defect, it is effective to previously avoid using a hose including an excessively degraded rubber layer, by regularly diagnosing a degrading situation of the hose, or predicting a remaining life until a use limit of the hose.

In view of such situation, we discovered that it is effective to measure a reaction force of the hose in order to diagnose the degrading situation of the hose.

Examples of a device for measuring the reaction force of the hose include a bending reaction force measuring device, which, when an elongated test hose with both ends fixed is bent into a semicircular shape between two points, measures the bending reaction force generated between the two points by using a detector disposed at either one of the two points (see JPH10-288575A (PTL1)).

CITATION LIST

Patent Literature

PTL1: JPH10-288575A

SUMMARY

Technical Problem

However, when measuring with a conventional bending reaction force measuring device, since a test hose is bent into a semicircular shape between the two points, in the case of measuring a bending reaction force of a hose for forming a flow path for transporting a fluid at high temperature and high pressure in construction machines, factory equipment, etc., it is necessary to respectively hold both ends thereof on a movable carriage. Therefore, a part of the hose for forming a flow path is necessarily cut out to prepare a test hose for this purpose.

Then, this disclosure aims to provide a reaction force measuring device, and a degradation diagnosing method and a degradation diagnosing device using the reaction force measuring device capable of measuring a reaction force of a hose for forming a flow path with the flow path staying formed without cutting the hose.

Solution to Problem

In order to achieve the aforementioned purpose, the reaction force measuring device according to this disclosure comprises: a receiving portion; a movable portion arranged in a manner spaced from the receiving portion and capable of moving toward the receiving portion, the movable portion having a sandwiching space formed between itself and the receiving portion, into which sandwiching space a hose can be inserted from a direction crossing a longitudinal direction of the hose; and a measuring portion configured to measure a reaction force of the hose sandwiched in the sandwiching space generated when the hose is pressed and applied with a load as the movable portion moves toward the receiving portion.

Advantageous Effect

According to this disclosure, it is possible to measure a reaction force of a hose for forming a flow path with the flow path staying formed without cutting the hose.

DETAILED DESCRIPTION

The following describes one of the disclosed embodiments with reference to drawings.

Figure 1:
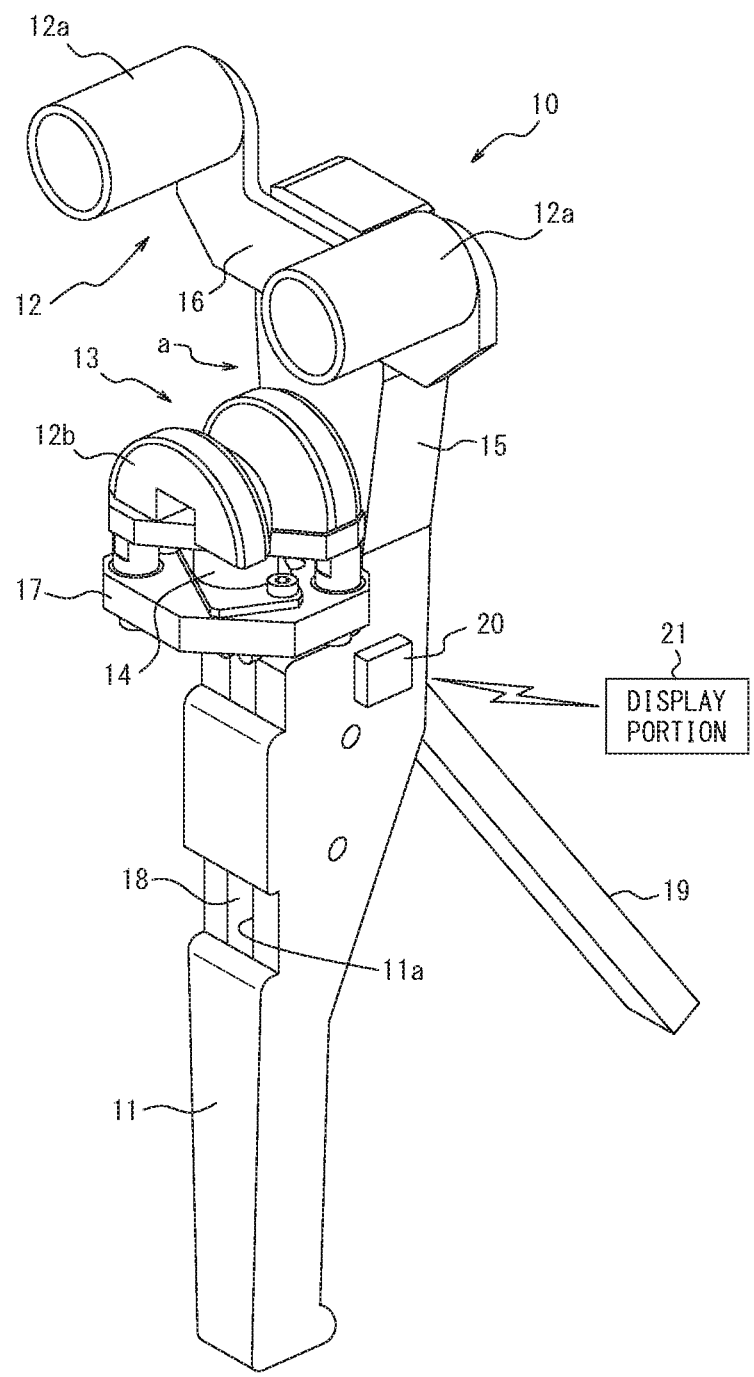
FIG. 1 illustrates a perspective view for schematically describing a reaction force measuring device according to one embodiment of this disclosure.
Figure 2:
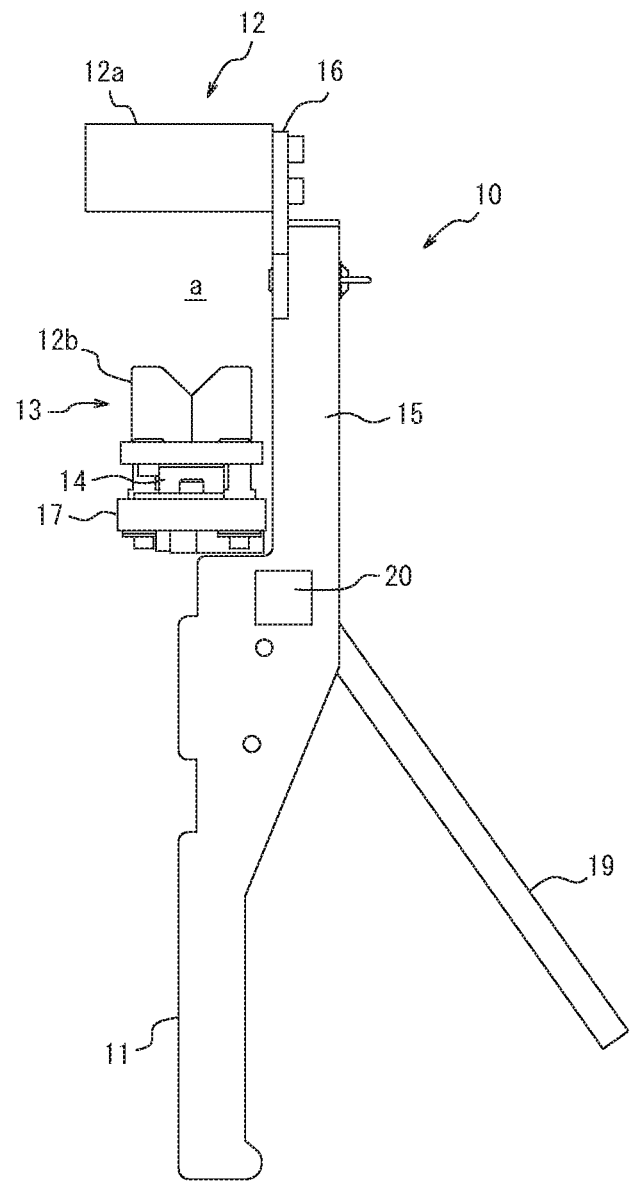
FIG. 2 illustrates a side view of the reaction force measuring device of FIG. 1.
Figure 3:
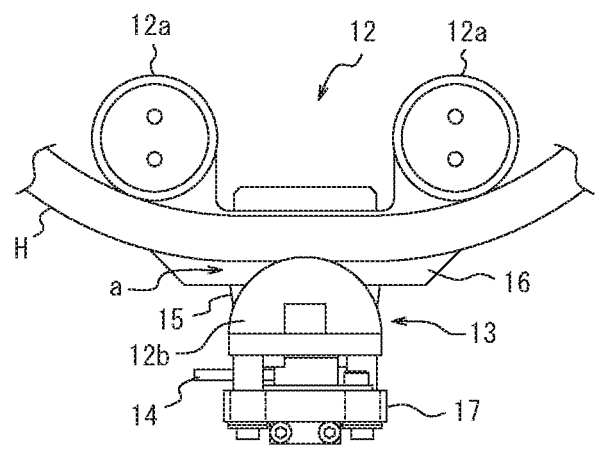
FIG. 3 partially describes the reaction force measuring device, and illustrates a state of the hose in the sandwiching space in FIG. 1.

As illustrated from FIG. 1 to FIG. 3, the reaction force measuring device 10 of the present embodiment is a device for measuring a reaction force in a hose H for forming a flow path. In this example, the reaction force measuring device 10 has a holding portion 11, a receiving portion 12 and a movable portion 13 arranged on an extended portion of the holding portion 11, and a measuring portion 14.

The hose H forms a flow path for transporting a fluid at high temperature and high pressure (e.g., oil), and is constituted by, e.g., respectively stacking from a radial inner side to an outer side an inner tube rubber layer, a metallic wire layer, an intermediate rubber layer, and an outer coating rubber layer. Note that a plurality of the metallic wire layers and the intermediate rubber layers may be respectively stacked alternately. This hose H is, for example, connected to a machine or device, etc. into which the fluid is transported by the hose H, via a metallic joint attached to both ends of the hose.

In the present example, the holding portion 11 is formed into a stick-like shape at a diameter holdable with one hand portably, and the shape and the weight of the entire reaction force measuring device 10 are set so as to be easily carried and held in a state where this holding portion 11 is held by an operator with one hand.

The receiving portion 12 is disposed at an end side of a sandwiching portion 15 composed of the extended portion extended along the holding portion 11, via a fixed base 16 attached detachably with, e.g., a toggle bolt. The movable portion 13 is disposed on a holding portion 11 side of the sandwiching portion 15 via a movable base 17, in a manner facing the receiving portion 12, spaced from the receiving portion 12 and capable of moving toward the receiving portion 12. The movable portion 13 is capable of moving together with the movable base 17 along the sandwiching portion 15, and forms a sandwiching space a between itself and the receiving portion 12, into which the hose H can be inserted in a direction crossing a longitudinal direction of the hose.

This receiving portion 12 is composed of two first guides 12a, 12a in, e.g., a cylindrical shape, which are spaced from each other along the hose H when the hose H is sandwiched in the sandwiching space a. The movable portion 13 is composed of one second guide 12b, which is located, when the hose H is sandwiched in the sandwiching space a, at a substantially intermediate position between the two first guides 12a, 12a, and is located on a side opposite to the receiving portion 12 across the hose H. The second guide 12b is formed into, e.g., a semi-cylindrical shape having a V-shaped groove at substantially an axial center. By arranging the receiving portion 12 composed of the two first guides 12a, 12a and the movable portion 13 composed of the one second guide 12b, it is possible to stably fix the hose when the hose is sandwiched and pressed.

In the present embodiment, the two first guides 12a, 12a are fixed to the fixed base 16, and the one second guide 12b is fixed to the movable base 17, but they may also be respectively rotatably attached with a central axis of a cylinder or a semi-cylinder as a rotation axis. Thereby, it is possible to reduce a frictional force between the hose H and each guide 12a, 12b, and thus it is possible to easily locate each guide 12a, 12b at any position on the hose H. Moreover, it is possible to form the first guides 12a into the same shape as the second guide 12b, or to form the second guide 12b into the same shape as the first guides 12a.

Figure 4:
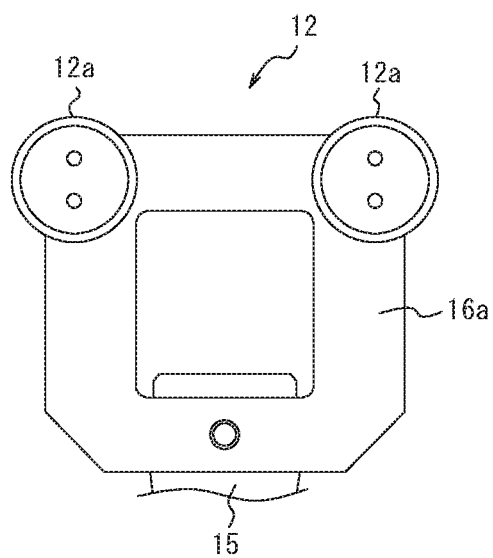
FIG. 4 describes another example of the fixed based in FIG. 1.

Moreover, as illustrated in FIG. 4, a large-size fixed base 16a may be used instead of the fixed base 16. The large-size base 16a is formed in a manner such that distances from its position to be attached to the sandwiching portion 15 to attachment positions of the two first guides 12a, 12a are longer than that of the fixed base 16. By using this large-size fixed base 16a, it is possible to elongate a distance between the receiving portion 12 and the movable portion 13, and to enlarge the sandwiching space a for sandwiching the hose H, which is compatible with a hose H with a large diameter.

Due to the receiving portion 12 composed of the two first guides 12a, 12a and the movable portion 13 composed of the one second guide 12b, in the reaction force measuring device 10, a groove-like recess opening to a surface side of the sandwiching portion 15 for attaching the receiving portion 12 and the movable portion 13 is formed between the receiving portion 12 and the movable portion 13. The hose H can be inserted in a direction crossing its longitudinal direction into the groove-like recess, and this groove-like recess becomes the sandwiching space a for sandwiching the hose H (see FIGS. 1 to 3).

Therefore, the reaction force measuring device 10 of the present embodiment is capable of locating the hose H in the sandwiching space a by pressing the reaction force measuring device 10 against the hose H from a side surface of the hose H so as to locate the hose H in the sandwiching space a. Thereby, it is possible to attach the reaction force measuring device 10 to the hose H, which is connected to a machine or device, etc. into which a fluid is to be transported, with the hose H staying connected. Therefore, it is possible to carry the reaction force measuring device 10 of the present embodiment to a location where it is necessary to perform the reaction force measurement of the hose H with it staying connected to a machine or device, etc., and to easily perform reaction force measurement of any place of the hose for forming a flow path, with the flow path staying formed without cutting the hose.

The movable base 17 attached to the movable portion 13 is integrated with one end of a rack 18 disposed to the holding portion 11. The rack 18 is attached slidably to a guide portion 11a (see FIG. 1) formed on the holding portion 11, which is in a groove-like shape along a longitudinal direction of the holding portion 11. The movable base 17 moves together with the rack 18 due to movement of the rack 18 upon operation to a handle 19 disposed on the holding portion 11.

In the present embodiment, the rack 18 and the handle 19 are constituted by a ratchet mechanism in which a movement direction of the rack 18 is limited to one direction, and are configured such that the rack 18 is capable of moving in a stepwise manner toward the receiving portion 12 upon operation to the handle 19. The handle 19 has one end pivotally supported by the holding portion 11, and the other end released and capable of being pushed toward the holding portion 11. Upon each operation pushing the handle 19, the rack 18 can be moved in a stepwise manner (one pitch each time). Upon movement of the rack 18, the movable portion 13 moves in a stepwise manner (one pitch each time) toward the receiving portion 12 together with the movable base 17 integrated with the rack 18.

In this way, upon operation to the handle 19, the movable portion 13 is moved, and a load is applied to the hose H sandwiched between itself and the receiving portion 12 in a stepwise manner by the ratchet mechanism, upon pressing movement of the movable portion 13. By applying the load to the hose H in a stepwise manner, it is possible to apply the load to the hose H in a stepwise manner at a constant pitch to the hose H, which enables accurate measurement of the applied load. Note that the present embodiment is not limited to the ratchet mechanism as long as it is possible to apply a load in a stepwise manner at a constant pitch.

Moreover, by performing an operation raising up the moved rack 18 toward the released other end side of the handle 19, e.g., in a direction opposite to a pushing direction, or by only releasing a pushing force, it is possible to release limitation of the movement direction and to restore the moved rack 18 to an original position before movement. By restoring the rack 18, it is possible to restore the movable portion 13 to an original position before movement.

Therefore, by operating the handle 19, as illustrated in FIG. 3, it is possible to perform pressing movement of the movable portion 13 by moving the movable portion 13 toward the hose H sandwiched in the sandwiching space a, so as to bring them in contact with each other, and further pressing the movable portion 13. Upon such pressing movement, the hose H comes into a load-applied state, i.e., a state where a pressed portion in contact with the movable portion 13 is bent to the pressing direction due to the applied load. The load applied to the hose H can be increased by increasing a pressing movement amount of the movable portion 13 toward the hose H.

In the present embodiment, a measuring portion 14 is attached to the movable portion 13 (see FIGS. 1 to 3). The measuring portion 14 is configured to measure the reaction force from the hose H sandwiched in the sandwiching space a generated when the hose H is pressed and applied with a load as the movable portion 13 moves toward the receiving portion 12. In the present embodiment, the measuring portion 14 uses a load cell. Namely, in the present embodiment, the measuring portion 14 is capable of measuring in the sandwiching space a a reaction force from the hose H, which is fixed at three points by the receiving portion 12 (the two first guides 12a, 12a) and the movable portion 13 (the one second guide 12b) and is in the load-applied state.

The load-applied state of the hose H of which the reaction force is measured by the measuring portion 14 is not limited to a state fixed at three points, as long as it is a state fixed by the receiving portion 12 and the movable portion 13 in which the hose H can be sandwiched and pressed from both sides. The receiving portion 12 is composed of at least one first guide 12a, and the movable portion 13 is composed of at least one second guide 12b located on a side opposite to the receiving portion 12 across the hose H when the hose H is sandwiched in the sandwiching space a. Moreover, three or more first guides 12a constituting the receiving portion 12 and two or more second guides 12b constituting the movable portion 13 may be disposed, and, for example, one first guide 12a of the receiving portion 12 and two second guides 12b of the movable portion 13 may be disposed, or the measuring portion 14 may be disposed on the receiving portion 12 side.

The reaction force measuring device 10 of the present embodiment has a display portion 21 configured to display a measurement result obtained by the measuring portion 14. The measurement result of the measuring portion 14 may be sent to the display portion 21 via wireless communication through, e.g., a wireless amplifier 20 (see FIGS. 1, 2) disposed on the holding portion 11, and may be displayed by the display portion 21 on, e.g., a liquid crystal display window as a reaction force data with respect to the load applied to the hose H as a measurement object. According to this configuration, the reaction force data measured by the measuring portion 14 can be directly certified from the display portion 21 as a measurement result.

The display portion 21 may be either disposed in a manner separated from the reaction force measuring device 10 (see FIG. 1) or disposed integrally with the reaction force measuring device 10. The measurement result may be sent from the measuring portion 14 to the display portion 21 via wired communication as well, without being limited to wireless communication via the wireless amplifier 20.

Note that in the present embodiment, FIG. 3 illustrates pressing movement of the movable portion 13 (the one second guide 12b) located on a bent portion outer surface of the hose H in a bent state when measuring the reaction force from the hose H, but the present disclosure is not so limited. When measuring the reaction force from the hose H, pressing movement may also be carried out with the movable portion 13 (the one second guide 12b) being located on a bent portion inner surface of the hose H in a bent state and the hose H being sandwiched between the movable portion 13 and the receiving portion 12 (the two first guides 12a, 12a) located on the bent portion outer surface of the hose H.

The reaction force of the hose H obtained via the reaction force measuring device 10 of the present embodiment may be effectively utilized for degradation diagnosis of the hose H.

Next, described is degradation diagnosis for investigating a degradation state of the hose H based on the reaction force data when the hose H as the measurement object is applied with a load, which is obtained via the reaction force measuring device 10 of the present embodiment.

The degradation state of the hose H as a diagnosis object may be used to predict, e.g., a remaining life of the hose H. The remaining life of the hose H may be predicted based on the reaction force data with respect to the hose H as a diagnosis object of the remaining life, which is obtained in the load-applied state of the hose H upon pressing movement of the movable portion 13 of the reaction force measuring device 10.

The remaining life of the hose H is predicted based on comparison of the reaction force data obtained in the load-applied state of the hose H and a testing result obtained previously with respect to a hose as a comparison object of the same type (caliber or internal structure, etc.) at a use limit state. This test is performed with respect to the hose as the comparison object under testing condition identical or comparatively close to the load applying test of the hose H as the diagnosis objects. The remaining life refers to a usage time remaining until the hose comes to the use limit state, while the degree at which the hose is degraded is defined as the use limit state may be appropriately set depending on the requirement.

The method for predicting the remaining life based on the comparison of the testing results with respect to the hoses as the diagnosis object and the comparison object may be any one. For example, by previously performing the load applying test under the same conditions respectively with respect to a plurality of hoses of the same type with different total usage times, tendency data indicating a correlation of the total usage time and the testing result of the load applying test is obtained. The obtained tendency data is preferably accumulated with respect to a plurality of types of hoses and testing conditions.

Next, by using those among the accumulated tendency data with the same type of the hose as the diagnosis object and testing conditions the same or comparatively close to the test performed with respect to the hose as the diagnosis object, the testing results of the hose as the diagnosis object and the testing result of the hose as the comparison object in the use limit state are compared. Based on such comparison, a degradation judgment table of the hose H is made.

Such degradation judgment table indicates a list of a judgment distinction such as "caution", "preferably not used" and the like based on reaction force values as an judgment standard and reaction force values as a measurement result, corresponding to the used pressure and caliber of each type of the hose H. By using this degradation judgment table, the reaction force data obtained in the load-applied state of the hose H upon pressing movement of the movable portion 13 of the reaction force measuring device 10, i.e., the reaction force values displayed by the display portion 21 as the measurement result obtained by the measuring portion 14 are compared. Due to the comparison, judgment corresponding to the reaction force values is obtained, and the degradation state of the hose as the diagnosis object based on the reaction force data values is judged.

Namely, by comparing the measurement result of the hose H as the diagnosis object obtained via the reaction force measuring device 10 and the accumulated tendency data, the accumulated tendency data being accumulated by performing load applying tests under the same conditions on a plurality of hoses of the same type as, but with different total usage times from, the hose H as the diagnosis object and obtaining the tendency data indicative of the correlation of the total usage times and the results of the load applying tests, it is possible to perform the degradation diagnosis of the hose H for judging the degradation state of the hose H as the diagnosis object.

Note that it is possible to incorporate the aforementioned degradation judgment based on the reaction force into an automatically executed program, and to integrally form a degradation judging portion providing the judgment result to the display portion 21, to thereby display the judgment result on the display portion 21. In this case, the degradation diagnosing device for the hose H is constituted by the reaction force measuring device 10 and the degradation judging portion.

Figure 5:
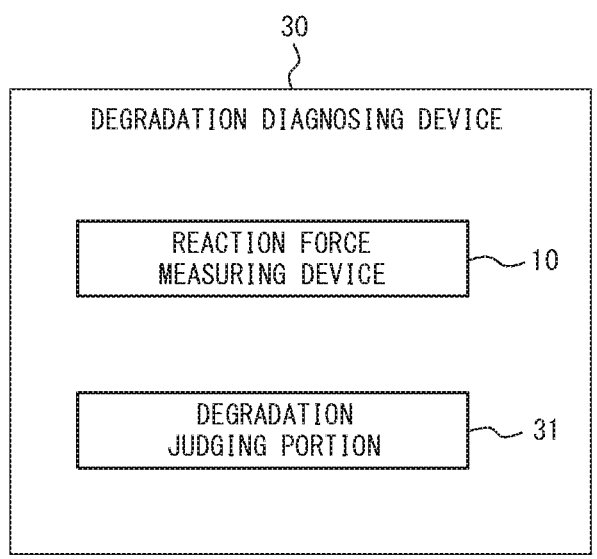
FIG. 5 illustrates a block chart showing a schematic configuration of an example of the degradation diagnosing device for hose.

FIG. 5 illustrates a block chart showing a schematic configuration of an example of the degradation diagnosing device for hose. As illustrated in FIG. 5, the degradation diagnosing device 30 for hose includes: a reaction force measuring device 10; and a degradation judging portion 31 configured to judge the degradation state of the hose H as the diagnosis object by comparing the measurement result of the hose H as the diagnosis object obtained with the reaction force measuring device 10 and the accumulated tendency data, the accumulated tendency data being accumulated by respectively performing load applying tests under the same conditions on a plurality of hoses of the same type as, but with different total usage times from, the hose H as the diagnosis object and obtaining the tendency data indicative of the correlation of the total usage times and the results of the load applying tests. Note that the degradation judging portion 31 may be, e.g., disposed independently without being formed integrally with the display portion 21.

In this way, the reaction force measuring device 10 according to this disclosure is capable of obtaining reaction force data of the hose H arranged on site such as construction machines or factory equipment, etc., as the measurement result of the measuring portion 14, via pressing movement of the movable portion 13, with the flow path staying formed by the hose H without cutting it. Moreover, according to the aforementioned embodiment, by forming at least the holding portion 11 into a stick-like shape with a diameter holdable with one hand, and thereby obtaining a configuration which is portable, or further, holdable with one hand, the reaction force measuring device 10 can be carried on site such as construction machines or factory equipment, etc. where the hose H for forming a flow path is disposed, and can be operated with one hand.

By using, e.g., the aforementioned degradation judgment table, from the reaction force data of the hose H obtained with the reaction force measuring device 10, it is possible to diagnose the degradation state of the hose H for forming a flow path which is arranged on site such as construction machines or factory equipment, etc. where the hose H is disposed with the flow path staying formed by the hose H without cutting it.

INDUSTRIAL APPLICABILITY

According to this disclosure, by using the reaction force measuring device, it is possible to obtain the reaction force data of the hose for forming a flow path in the load-applied state upon pressing movement with the flow path staying formed without cutting the hose, and it is possible to judge the degradation state of the hose by using the degradation judgment table from this reaction force data. Therefore, it is preferably used in the case where the degradation diagnosis of the hose arranged on site such as construction machines or factory equipment, etc. is performed in used.

REFERENCE SIGNS LIST 10 reaction force measuring device
11 holding portion
11a guide portion
12 receiving portion
12a first guide
12b second guide
13 movable portion
14 measuring portion
15 sandwiching portion
16 fixed base
16a large-size fixed base
17 movable base
18 rack
19 handle
20 wireless amplifier
21 display portion
30 degradation diagnosing device
31 degradation judging portion
H hose
a sandwiching space

The invention claimed is:
1. A reaction force measuring device comprising:
a receiving portion;
a movable portion arranged in a manner spaced from the receiving portion and capable of moving toward the receiving portion, the movable portion having a sandwiching space formed between itself and the receiving portion, into which sandwiching space a hose can be inserted from a direction crossing a longitudinal direction of the hose;
a measuring portion configured to measure a reaction force of the hose sandwiched in the sandwiching space generated when the hose is pressed and applied with a load as the movable portion moves toward the receiving portion; and
an opening adjacent the sandwiching space that permits insertion of the hose, and which remains open along a full length of the hose extending between the receiving portions and movable portion when the hose is pressed and applied with the load.
2. The reaction force measuring device according to claim 1, wherein:
the receiving portion comprises at least one first guide, and the movable portion comprises at least one second guide located, when the hose is sandwiched in the sandwiching space, on a side opposite to the receiving portion across the hose.

3. The reaction force measuring device according to claim 2, wherein:
the movable portion is moved toward the receiving portion in a stepwise manner by a ratchet mechanism.

4. The reaction force measuring device according to claim 3, further comprising a display portion configured to display a measurement result obtained by the measuring portion.

5. A degradation diagnosing method, comprising:
judging a degradation state of a hose as a diagnosis object by comparing a measurement result of the hose as the diagnosis object obtained with the reaction force measuring device according to claim 3 and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and the results of the load applying tests.

6. A degradation diagnosing device, comprising:
the reaction force measuring device according to claim 3; and
a degradation judging portion configured to judge a degradation state of a hose as a diagnosis object by comparing a measurement result of the hose as the diagnosis object obtained with the reaction force measuring device and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and results of the load applying tests.

7. The reaction force measuring device according to claim 2, further comprising a display portion configured to display a measurement result obtained by the measuring portion.

8. A degradation diagnosing method, comprising:
judging a degradation state of a hose as a diagnosis object by comparing a measurement result of the hose as the diagnosis object obtained with the reaction force measuring device according to claim 7 and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and the results of the load applying tests.

9. A degradation diagnosing method, comprising:
judging a degradation state of a hose as a diagnosis object by comparing a measurement result of the hose as the diagnosis object obtained with the reaction force measuring device according to claim 2 and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and the results of the load applying tests.

10. A degradation diagnosing device, comprising:
the reaction force measuring device according to claim 2; and
a degradation judging portion configured to judge a degradation state of a hose as a diagnosis object by comparing a measurement result of the hose as the diagnosis object obtained with the reaction force measuring device and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and results of the load applying tests.

11. The reaction force measuring device according to claim 1, wherein:
the movable portion is moved toward the receiving portion in a stepwise manner by a ratchet mechanism.

12. The reaction force measuring device according to claim 11, further comprising a display portion configured to display a measurement result obtained by the measuring portion.

13. A degradation diagnosing method, comprising:
judging a degradation state of a hose as a diagnosis object by comparing a measurement result of the hose as the diagnosis object obtained with the reaction force measuring device according to claim 11 and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and the results of the load applying tests.

14. A degradation diagnosing device, comprising:
the reaction force measuring device according to claim 11; and
a degradation judging portion configured to judge a degradation state of a hose as a diagnosis object by comparing a measurement result of the hose as the diagnosis object obtained with the reaction force measuring device and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and results of the load applying tests.

15. The reaction force measuring device according to claim 1, further comprising a display portion configured to display a measurement result obtained by the measuring portion.

16. A degradation diagnosing method, comprising:
judging a degradation state of a hose as a diagnosis object by comparing a measurement result of the hose as the diagnosis object obtained with the reaction force measuring device according to claim 15 and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and the results of the load applying tests.

17. A degradation diagnosing device, comprising:
the reaction force measuring device according to claim 15; and
a degradation judging portion configured to judge a degradation state of a hose as a diagnosis object by comparing a measurement result of the hose as the diagnosis object obtained with the reaction force measuring device and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and results of the load applying tests.

18. A degradation diagnosing method, comprising:
judging a degradation state of a hose as a diagnosis object by comparing a measurement result of the hose as the diagnosis object obtained with the reaction force measuring device according to claim 1 and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and the results of the load applying tests.

19. A degradation diagnosing device, comprising:
the reaction force measuring device according to claim 18; and
a degradation judging portion configured to judge a degradation state of a hose as a diagnosis object by comparing a measurement result of the hose as the diagnosis object obtained with the reaction force measuring device and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and results of the load applying tests.

20. A degradation diagnosing device, comprising:
the reaction force measuring device according to claim 1; and
a degradation judging portion configured to judge a degradation state of a hose as a diagnosis object by comparing a measurement result of the hose as the diagnosis object obtained with the reaction force measuring device and accumulated tendency data, the accumulated tendency data being accumulated by respectively performing load applying tests under the same conditions on a plurality of hoses of the same type as, but with different total usage times from, the hose as the diagnosis object and obtaining tendency data indicative of a correlation of the total usage times and results of the load applying tests.

* * * * *